US008469961B2

(12) United States Patent
Alleyne et al.

(10) Patent No.: US 8,469,961 B2
(45) Date of Patent: Jun. 25, 2013

(54) METHODS AND COMPOSITIONS FOR MINIMALLY INVASIVE CAPSULAR AUGMENTATION OF CANINE COXOFEMORAL JOINTS

(76) Inventors: Neville Alleyne, La Jolla, CA (US); Stuart Young, Del Mar, CA (US)

( * ) Notice: Subject to any disclaimer, the term of this patent is extended or adjusted under 35 U.S.C. 154(b) by 888 days.

(21) Appl. No.: 12/398,124

(22) Filed: Mar. 4, 2009

(65) Prior Publication Data
US 2010/0004699 A1  Jan. 7, 2010

Related U.S. Application Data

(60) Provisional application No. 61/034,118, filed on Mar. 5, 2008.

(51) Int. Cl.
*A61F 2/46* (2006.01)
(52) U.S. Cl.
USPC ...................................... 606/86 R; 623/23.58
(58) Field of Classification Search
USPC ....................................................... 623/23.58
See application file for complete search history.

(56) References Cited

U.S. PATENT DOCUMENTS

| | | |
|---|---|---|
| 2,474,911 A | 7/1949 | Pierce et al. |
| 4,526,909 A | 7/1985 | Urist |
| 4,837,285 A | 6/1989 | Berg et al. |
| 5,024,659 A | 6/1991 | Sjostrom |
| 5,134,122 A | 7/1992 | Orsolini |
| 5,171,279 A | 12/1992 | Mathews |
| 5,258,028 A | 11/1993 | Ersek et al. |
| 5,286,763 A | 2/1994 | Gerhart et al. |
| 5,290,271 A | 3/1994 | Jernberg |
| 5,344,452 A | 9/1994 | Lemperle |
| 5,352,715 A | 10/1994 | Wallace et al. |
| 5,571,182 A | 11/1996 | Ersek et al. |
| 5,599,852 A | 2/1997 | Scopelianos et al. |
| 5,641,514 A | 6/1997 | Cho |
| 5,922,025 A | 7/1999 | Hubbard |
| 6,107,466 A | 8/2000 | Hasan et al. |
| 6,129,761 A | 10/2000 | Hubbell |
| 6,160,033 A | 12/2000 | Nies |

(Continued)

FOREIGN PATENT DOCUMENTS

| | | |
|---|---|---|
| EP | 1410810 | 4/2004 |
| JP | 5-508795 | 12/1993 |

(Continued)

OTHER PUBLICATIONS

Arshady, Reza, "Preparation of biodegradable microspheres and microcapsules: 2. Polyactides and related polyesters" *J. Controlled Release* (1991) 17: 1-22.

(Continued)

*Primary Examiner* — Thomas J Sweet
*Assistant Examiner* — Matthew Schall
(74) *Attorney, Agent, or Firm* — Knobbe Martens Olson & Bear LLP

(57) ABSTRACT

The present technology relates to methods and devices for augmenting the canine coxofemoral joint. In particular, methods for augmenting the capsule of the canine coxofemoral joint are provided. In some embodiments, augmentation can be performed by injecting an implantable device comprising a biodegradable matrix and microparticles into the capsule. In some embodiments, augmentation can be performed by imbricating an implantable device comprising a biodegradable matrix and microparticles at the capsule.

28 Claims, 3 Drawing Sheets

U.S. PATENT DOCUMENTS

| | | | |
|---|---|---|---|
| 6,183,518 | B1 | 2/2001 | Ross et al. |
| 6,264,659 | B1 | 7/2001 | Ross et al. |
| 6,264,695 | B1 | 7/2001 | Stoy |
| 6,284,872 | B1 | 9/2001 | Celeste et al. |
| 6,309,420 | B1 | 10/2001 | Preissman |
| 6,335,028 | B1 | 1/2002 | Vogel et al. |
| 6,355,705 | B1 | 3/2002 | Bond et al. |
| 6,383,200 | B1 | 5/2002 | Wotton, III |
| 6,391,059 | B1 | 5/2002 | Lemperle et al. |
| 6,432,437 | B1 | 8/2002 | Hubbard |
| 6,468,274 | B1 | 10/2002 | Alleyne et al. |
| 6,652,883 | B2 | 11/2003 | Goupil et al. |
| 6,713,527 | B2 | 3/2004 | Bond et al. |
| 7,060,103 | B2 | 6/2006 | Carr et al. |
| 7,131,997 | B2 | 11/2006 | Bourne |
| 7,306,627 | B2 | 12/2007 | Tanagho et al. |
| 7,341,601 | B2 | 3/2008 | Eiserman et al. |
| RE41,286 | E | 4/2010 | Atkinson et al. |
| 8,127,770 | B2 | 3/2012 | Alleyne et al. |
| 2002/0045942 | A1 | 4/2002 | Ham |
| 2002/0176893 | A1 | 11/2002 | Wironen et al. |
| 2003/0009235 | A1 | 1/2003 | Manrique et al. |
| 2003/0149490 | A1 | 8/2003 | Ashman |
| 2003/0158607 | A1 | 8/2003 | Carr et al. |
| 2003/0211083 | A1 | 11/2003 | Vogel et al. |
| 2003/0236573 | A1 | 12/2003 | Evans et al. |
| 2004/0024465 | A1 | 2/2004 | Lambrecht et al. |
| 2004/0054414 | A1 | 3/2004 | Trieu et al. |
| 2004/0115240 | A1 | 6/2004 | Narhi et al. |
| 2005/0031666 | A1 | 2/2005 | Trieu |
| 2005/0100510 | A1 | 5/2005 | Falco |
| 2006/0002971 | A1 | 1/2006 | Saltzman et al. |
| 2006/0052795 | A1 | 3/2006 | White |
| 2006/0074423 | A1 | 4/2006 | Alleyne et al. |
| 2006/0074424 | A1 | 4/2006 | Alleyne et al. |
| 2006/0093644 | A1 | 5/2006 | Quelle et al. |
| 2006/0206116 | A1 | 9/2006 | Yeung |
| 2006/0263830 | A1 | 11/2006 | Grinstaff et al. |
| 2008/0096976 | A1 | 4/2008 | Alleyne |
| 2008/0124371 | A1 | 5/2008 | Turos et al. |
| 2008/0160060 | A1* | 7/2008 | Ellies .......................... 424/422 |
| 2008/0166386 | A1 | 7/2008 | Caseres et al. |
| 2008/0299172 | A1 | 12/2008 | Young et al. |
| 2009/0074728 | A1 | 3/2009 | Gronthos et al. |
| 2010/0004700 | A1 | 1/2010 | Alleyne |
| 2010/0010549 | A1 | 1/2010 | Alleyne et al. |
| 2010/0316715 | A1 | 12/2010 | Andersson |
| 2011/0230919 | A1 | 9/2011 | Alleyne |

FOREIGN PATENT DOCUMENTS

| | | |
|---|---|---|
| JP | 2002-505308 | 2/2002 |
| WO | WO 92/10982 | 7/1992 |
| WO | WO 98/40113 | 9/1998 |
| WO | WO99/44643 | 9/1999 |
| WO | WO 00/44808 | 8/2000 |
| WO | WO 0044394 | 8/2000 |
| WO | WO 02/04007 | 5/2002 |
| WO | WO 02/062404 | 8/2002 |
| WO | WO 03/049669 | 6/2003 |
| WO | WO 2004/026189 | 4/2004 |
| WO | WO 2005/046746 | 5/2005 |
| WO | WO 2008/005676 | 1/2008 |

OTHER PUBLICATIONS

"Clinical Practice Guideline: Early Detection of Developmental Dysplasia of the Hip" *Pediatrics* (2000) 105(4): 896-905.

Holland, et al., "Polymers for Biodegradable Medical Devices. 1. The Potential of Polyesters as Controlled Macromolecular Release Systems" *J. Controlled Release* (1986) 4: 155-180.

Konde, et al., "Radiographic Evaluation of Total Hip Replacement in the Dog" *Veterinary Radiology* (1982) 23(3): 98-106.

Liska, William D., "Femur Fractures Associated with Canine Total Hip Replacement" *Veterinary Surgery* (2004) 33: 164-172.

Martini, et al., "Extra-articular Absorbable Suture Stabilization of Coxofemoral Luxation in Dogs" *Veterinary Surgery* (2001) 30: 468-475.

Miller, et al., "Collagen: An Overview" *Methods in Enzymology* (1982) 82: 3-32.

Montgomery, et al., "Total Hip Arthroplasty for Treatment of Canine Hip Dysplasia" *Veterinary Clinics of North America: Small Animal Practice* (1992) 22(3): 703-719.

Olmstead, Marvin L., "Total Hip Replacement" *Veterinary Clinics of North America: Small Animal Practice* (1987) 17(4): 943-955.

Olmstead, Marvin L., "Total Hip Replacement in the Dog" *Seminars in Veterinary Medicine and Surgery (Small Animal)* (1987) 2(2): 131-140.

Pitt, C. G., "The controlled parenteral delivery of polypeptides and proteins" *Intl. J. Pharma.* (1990) 59: 173-196.

Richardson, Daniel C., "The Role of Nutrition in Canine Hip Dysplasia" *Veterinary Clinics of North America: Small Animal Practice* (1992) 22(3): 529-540.

Tomlinson, et al. "Total hip replacement: The best treatment for dysplastic dogs with osteoarthrosis" *Veterinary Medicine* (1996): 118-124.

Artecoll Product History. Downloaded from www.artecoll.com on Jun. 2, 2010, pp. 1-2.

Bayston, et al., "The sustained release of antimicrobial drugs from bone cement. An appraisal of laboratory investigations and their significance," *J. Bone Joint Surg.* (Br), (1982), 64(4):460-464.

Cohen et al., Artecoll—A Long-Lasting Injectable Wrinkle Filler Material: Report of a Controlled, Randomized, Multicenter Clinical Trial of 251 Subjects, Plastic Reconst. Surg., (2004), vol. 114(4), 964-976.

Carruthers, Artecoll® —an injectable micro-implant for longlasting soft tissue augmentation, Skin Therapy Letter, (1999), vol. 4(2), 1-2.

Faught, et al., "The effects of laser energy on the arterial wall." Annals of Vascular Surgery 4 (1990); 198-207.

Masala, et al., Percutaneous Vertebroplasty in Painful Schmorl Nodes, Cardio Vascular and International Radiology, (2006), vol. 29, 97-101.

Wahlig, et al., "Pharmacokinetic study of gentamicin-loaded cement in total hip replacements. Comparative effects of varying dosage," *J. Bone Joint Surg.* (Br), (1984), 66(2):175-179.

Office Action dated Dec. 7, 2010 in U.S. Appl. No. 12/132,557.

Office Action dated Aug. 31, 2011 in U.S. Appl. No. 12/132,557.

\* cited by examiner

METHODS AND COMPOSITIONS FOR MINIMALLY INVASIVE CAPSULAR AUGMENTATION OF CANINE COXOFEMORAL JOINTS

CROSS-REFERENCE TO RELATED APPLICATIONS

This application claims priority to U.S. Provisional Application No. 61/034,118, entitled "A Device and Method for Minimally Invasive Capsular and Augmentation for Canine Coxofemoral Joint," filed on Mar. 5, 2008, which is hereby incorporated by reference in its entirety.

FIELD OF THE INVENTION

The present technology relates to the field of veterinary medicine. In particular, methods and devices are provided for augmenting the capsule of the canine coxofemoral joint.

BACKGROUND

Hip dysplasia is a common problem in veterinary practice, accounting for up to 30% of canine orthopedic cases (Richardson D. C. "The role of nutrition in canine hip dysplasia." Vet Clin North Am Small Anim. Pract. 1992; 22: 529-540). The frequency of the disease varies among breeds and can be as high as 70.5% in bulldogs and 48.2% in St. Bernards (Corley E. A, Keller G. G. "Hip Dysplasia: A Progress Report and Update." Columbia, Mo.: Orthopedic Foundation of Animals 1993 (suppl)). Male and female dogs are affected with equal frequency, in contrast to the disease in humans, where 80% of cases are female (Committee on Quality Improvement, Subcommittee on Developmental Dysplasia of the Hip "Clinical Practice Guideline: Early Detection of Developmental Dysplasia of the Hip" Pediatrics (2000) 105: 896-905).

The canine coxofemoral joint is a ball and socket joint, where the femoral head meets the socket of the acetabulum. In chronic canine hip dysplasia, the joint becomes deformed where the femoral head is subluxed out of the joint resulting in significant pain, restricted range of motion, and accelerated osteoarthritic changes of the joint.

Treatment for canine hip dysplasia can include total hip replacement. Total hip replacement has become one of the most successful procedures utilized in the treatment of canine hip dysplasia, and associated disorders such as coxarthrosis; severe osteoarthritis, chronic subluxation, avascular necrosis, and fracture dislocation. The typical minimum age for total hip replacement is approximately 10 months and/or a body weight of 35 pounds, and there appears to be no upper age limit for total hip replacement (Olmstead M L. "Total hip replacement." Vet Clin North Am Small Anim Pract 1987, 17, 943-955; Tomlinson J, McLaughlin R Jr. "Total hip replacement: The best treatment for dysplastic dogs with osteoarthrosis. Symposium on CHD: Surgical Management." Vet Med 1996, 91, 118-124; and Olmstead M L. "Total hip replacement in the dog." Semin Vet Med Surg (Small Anim) 1987, 2, 131-140). However, total hip replacement can lead to complications such as aseptic loosening, chronic subluxation, nerve injury, infection, fracture of the acetabulum, fracture of the femoral stem or shaft, patella luxation, pulmonary embolism and death (Konde L J, et al. "Radiographic evaluation of total hip replacement in the dog." Vet Radiol 1982, 20, 98-106; Liska W D. "Femur fractures associated with canine total hip replacement." Vet Surg 2004, 33, 164-172; and Montgomery R D et al. "Total hip arthroplasty for treatment of canine hip dysplasia." Vet Clin North Am Small Anim Pract 1992, 22, 703-719).

Despite expensive screening and breeding programs, the disease continues to have a major economic and emotional impact on dog breeders and owners. Accordingly, there is a need for minimally invasive methods and devices to treat hip dysplasia and associated disorders.

SUMMARY

The present technology relates to methods and devices for augmenting the capsule of a canine coxofemoral joint. Some methods described herein can include the steps of identifying a subject in need of capsular augmentation, delivering an implantable device to the capsule, in which the implantable device includes a biodegradable matrix and a plurality of microparticles, and contacting the implantable device with at least a portion of the capsule.

In some methods for augmenting the capsule of a canine coxofemoral joint, the implantable device can include a sheet. In some such embodiments, the sheet can include fenestrations. More methods can also include anchoring the implantable device at the joint. In certain embodiments, the anchoring can be at one or more sites of the joint selected from the capsule, iliofemoral ligament, ischiocapsular ligament, pubocapsular ligament, acetabular labrum, ligamentum teres femoris, acetabulum, or femoral neck.

In some methods for augmenting the capsule of a canine coxofemoral joint, delivering can include injecting the implantable device into one or more sites of the capsule. In some such methods, one or more sites can be selected from the capsule, iliofemoral ligament, ischiocapsular ligament, pubocapsular ligament. acetabular labrum, and ligamentum teres femoris. In more embodiments, the injecting can be into at least a portion of the stratum fibrosum of the capsule.

In some methods for augmenting the capsule of a canine coxofemoral joint, contacting the implantable device with at least a portion of the joint can include at least a portion of one or more sites selected from the capsule, iliofemoral ligament, ischiocapsular ligament, pubocapsular ligament, acetabular labrum, and ligamentum teres femoris.

In some methods for augmenting the capsule of a canine coxofemoral joint, the joint has undergone capsulotomy or partial capsulectomy.

In some methods for augmenting the capsule of a canine coxofemoral joint, delivering includes percutaneous delivery. In some methods for augmenting the capsule of a canine coxofemoral joint, delivering includes an open surgical procedure.

In some methods for augmenting the capsule of a canine coxofemoral joint, the biodegradable matrix includes bovine collagen.

In some methods for augmenting the capsule of a canine coxofemoral joint, the biodegradable matrix includes one or more materials selected from albumin, gelatin, chitosan, hyaluronic acid, starch, cellulose, cellulose derivatives (e.g. methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D, L lactide), poly (D, L-lactide-co-glycolide), poly(glycolide), poly(hydroxybutyrate), poly(alkylcarbonate), poly(orthoesters), polyesters, poly(hydroxyvaleric acid), polydioxanone, poly(ethylene terephthalate), poly (malic acid), poly(tartronic acid), polyanhydrides, polyphosphazenes, poly(amino acids), and copolymers thereof.

In some methods for augmenting the capsule of a canine coxofemoral joint, the plurality of microparticles include a material selected from the group consisting of poly methacrylate, polymethyl methacrylate, hydroxapatite, powdered bone, and glass.

In some methods for augmenting the capsule of a canine coxofemoral joint, the plurality of microparticles can be substantially spherical with a diameter less than 200 µm. In more embodiments, the plurality of microparticles can be substantially spherical with a diameter less than 100 µm.

In some methods for augmenting the capsule of a canine coxofemoral joint, the implantable device can also include a bioactive agent. In more embodiments, the bioactive agent can include an agent selected from the group consisting of a local anesthetic, non-steroidal anti-inflammatory drug, antibiotic, and antineoplastic agent. In more embodiments, the bioactive agent can include lidocaine.

In some methods for augmenting the capsule of a canine coxofemoral joint, the implantable device can also include a substrate. In more embodiments, the substrate can include a material selected from nylon, Dacron, and Teflon. In more embodiments, the substrate can be coated with the plurality of microparticles and the biodegradable matrix.

In addition to the methods described herein, also provided is a canine coxofemoral joint including an implantable device, in which the implantable device comprises collagen and microparticles.

In some embodiments, the collagen comprises bovine collagen.

In some embodiments, the microparticles are substantially spherical with a diameter less than 200 µm. In more embodiments, the microparticles are substantially spherical with a diameter less than 100 µm.

In some embodiments, the implantable device further comprises a bioactive agent. In more embodiments, the bioactive agent comprises an agent selected from the group consisting of a local anesthetic, non-steroidal anti-inflammatory drug, antibiotic, and antineoplastic agent. In more embodiments, the bioactive agent comprises lidocaine.

DETAILED DESCRIPTION

The present invention relates to methods and devices for augmenting the capsule of a canine coxofemoral joint. In particular embodiments, methods are provided that include identifying a subject in need of capsular augmentation, delivering an implantable device to the capsule, in which the implantable device includes a biodegradable matrix and a plurality of microparticles, and contacting the implantable device with at least a portion of the capsule are described. Such methods and devices can be useful to treat canine hip dysplasia and related disorders.

In some embodiments, the implantable device can include a biodegradable matrix, such as collagen, and microparticles comprised of polymethyl methacrylate (PMMA). The device can be inserted at the canine coxofemoral to augment the capsule. Without wishing to be bound to any one theory, it is believed that the biodegradable matrix provides a substrate for the host's fibroblasts to migrate into the device and invoke a fibrotic response at the insertion site. In addition, the microparticles may further invoke the host to secrete components of the extracellular matrix, including the host's own collagen, at the site of insertion. Thus the response to inserting such an implantable device at the canine coxofemoral capsule can be that the host produces a fibrous matrix at the site of insertion, thickening and tightening the capsule, and strengthening the joint. Moreover, as the host continues to produce a fibrous matrix at the site of insertion, the tensile strength at the site of insertion can increase with time. This is in contrast to hip repairs such as arthroplasty, which tend to become weaker over a period of time through loosening of cement, stem migration or sublimation, and infection.

Figure 1:
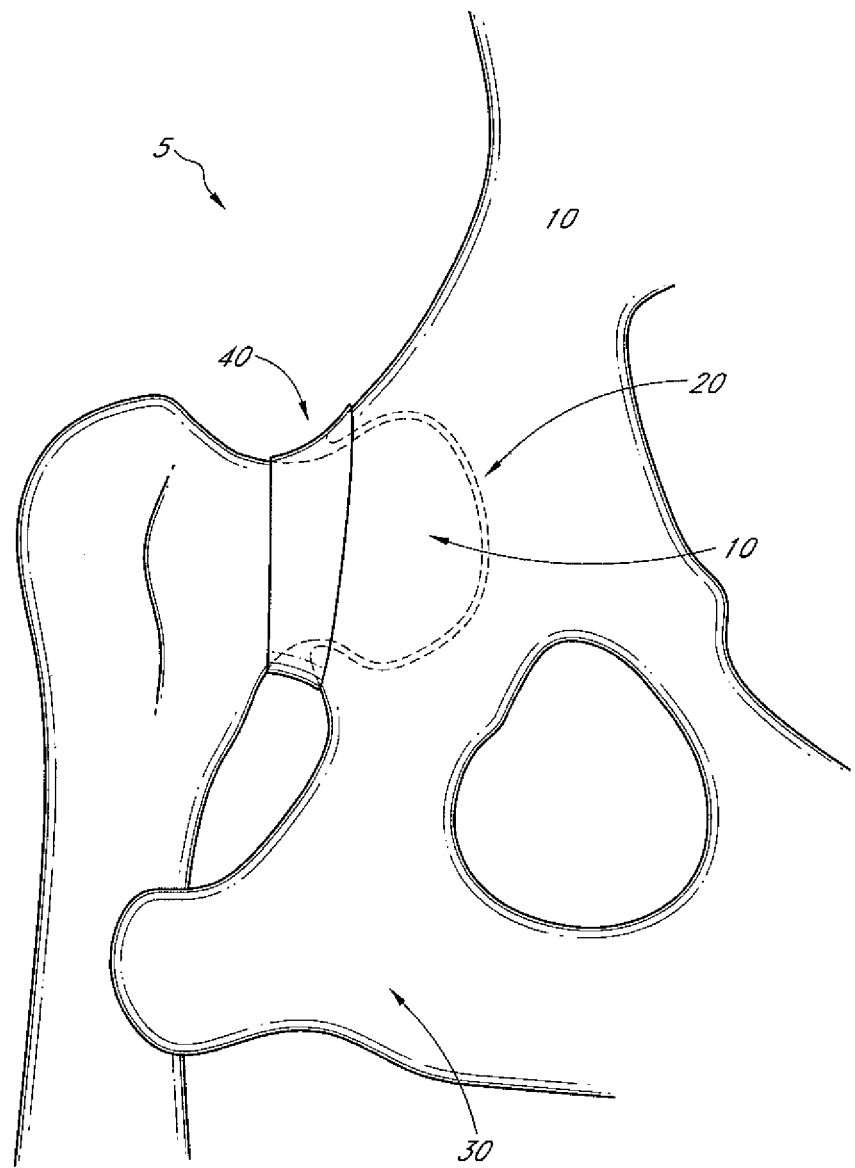
FIG. 1 shows a schematic of a canine coxofemoral joint (5). The joint includes the femoral head (10), the acetabulum (20), pelvis (30), and capsule (40).

Referring to FIG. 1, the canine coxofemoral joint (5) includes the femoral head (10) which is used for articulation of the joint. The acetabulum (20) represents the concave portion of the coxofemoral joint and is part of the pelvis (30). The deep acetabulum is further extended by a band of fibrocartilage surrounding its rim. This acetabular lip is continued as a transverse acetabular ligament in the ventral aspect of the femur and completes the circular restraint of the hip joint. The ligament of the head of the femur, also known as the teres ligament or round ligament, is a short, flat ligament that connects the center of the femoral head to the acetabular fossa. This ligament contributes to femoral stability by retaining the femoral head within the acetabulum and in the adult dog provides some vascularity to the femoral head. The coxofemoral joint is surrounded by a fibrous joint capsule (40) that is connected to the femur at the base of the neck and at the acetabulum just around the acetabular lip. In chronic canine hip dysplasia, the joint becomes deformed where the femoral head is subluxed out of the joint. In such cases, the capsule of the coxofemoral joint can be one of the only restraining structures to maintain containment.

Figure 2:
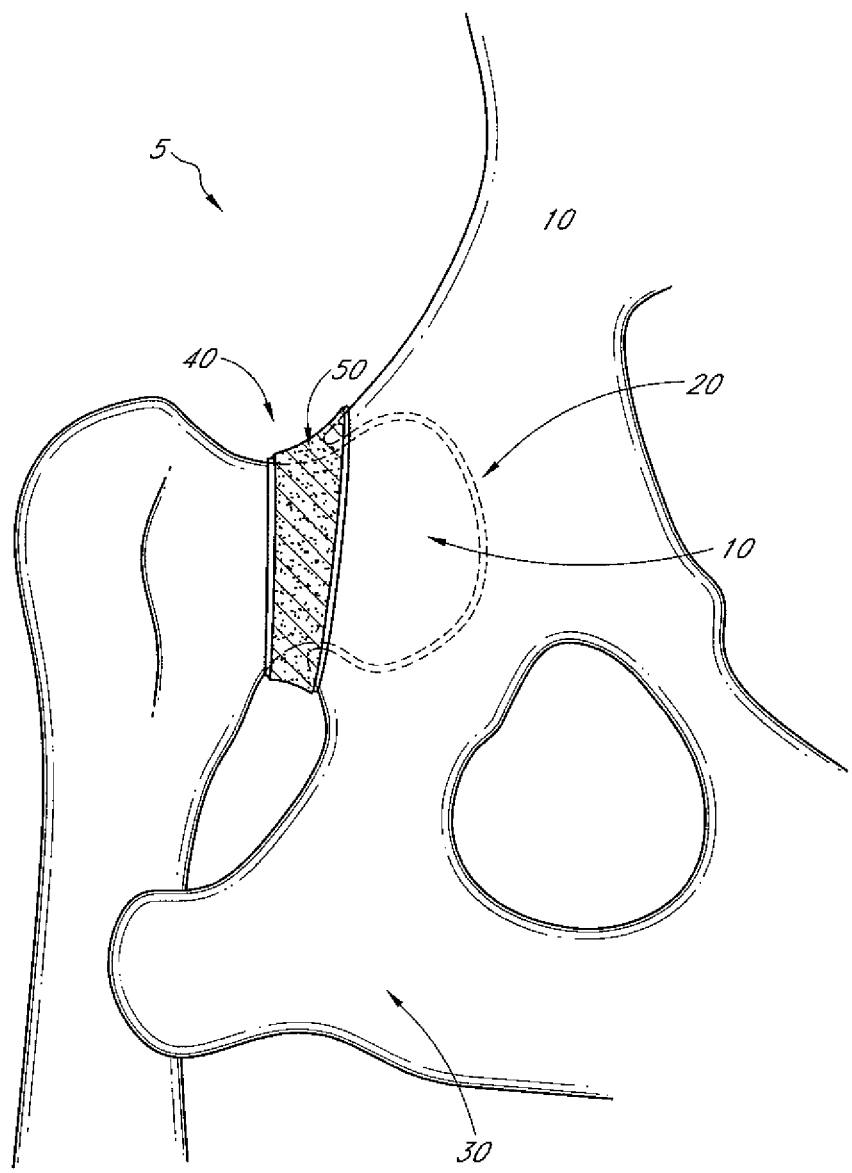
FIG. 2 shows a schematic of a canine coxofemoral joint imbricated with a collagen mesh containing microparticles.

In some methods to augment a canine capsule (40), an implantable solid mesh described herein. Referring now to FIG. 2, for example, a collagen mesh (50) containing microparticles can be wrapped around the capsule of a canine coxofemoral joint. The mesh can be imbricated to the capsule. Because the capsule may not be invaded, this method has the advantage of being minimally invasive. Thus the veterinary surgeon can minimize her incision on the capsule, reducing blood loss, and minimizing articular destruction, as compared to more invasive methods. Moreover, wrapping the capsule with the mesh strengthens the joint two-fold. First, the mesh provides tensile strength to the capsule, and second, the tensile strength increases as the biodegradable collagen is replaced by the host's collagen and secretions.

Figure 3:
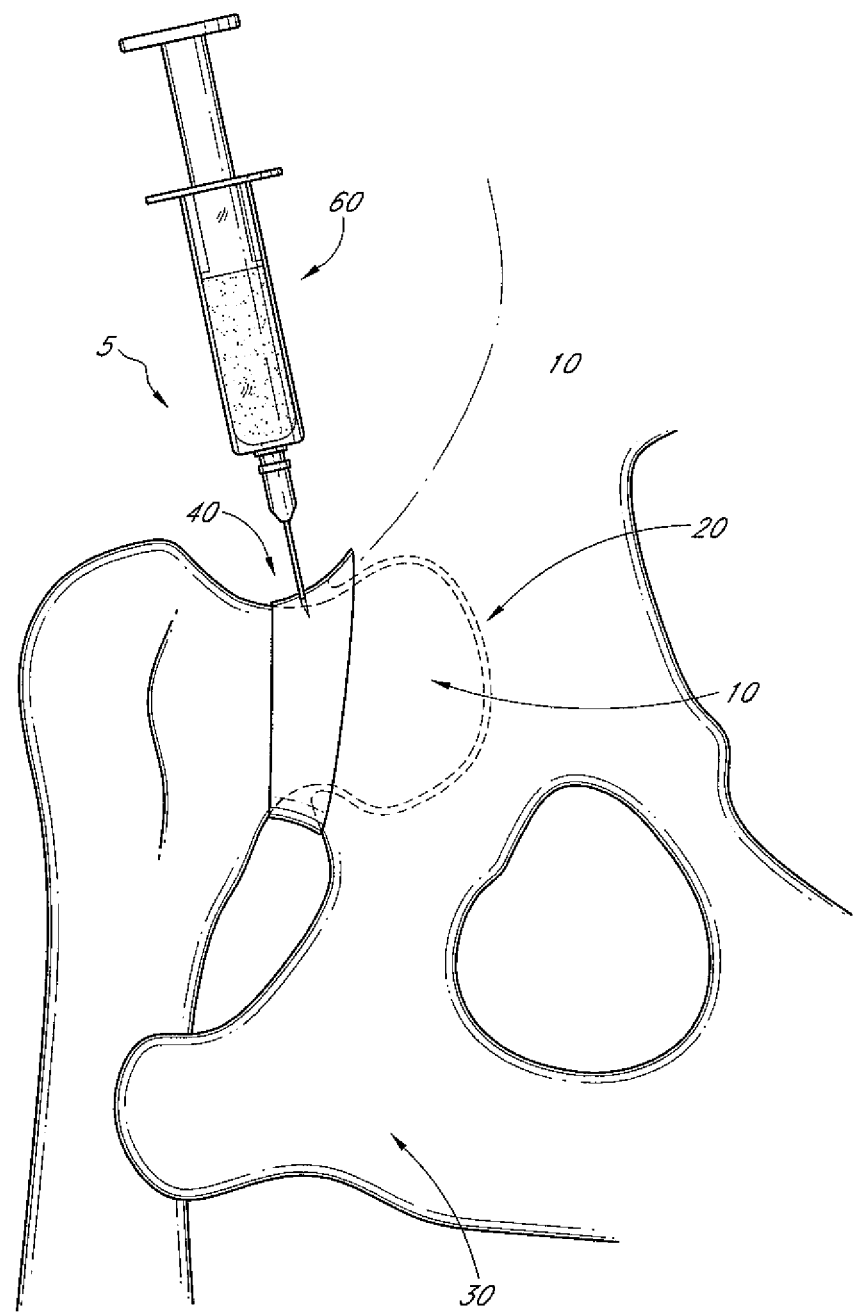
FIG. 3 shows a schematic of a canine coxofemoral joint injected with a collagen matrix containing microparticles.

In other embodiments, the implantable device can be in the form of a fluid gel or paste. Such devices can be injected into a coxofemoral capsule. Referring to FIG. 3, the implantable devices described herein can be injected into the capsule using a syringe (60). As will be apparent, methods including injecting the implantable device are particularly advantageous because the treatment is minimally invasive.

The following description is directed to certain specific embodiments. However, the invention can be embodied in a multitude of different ways. Reference in this specification to "one embodiment" or "an embodiment" means that a particular feature, structure, or characteristic described in connection with the embodiment is included in at least one embodiment. The appearances of the phrase "in one embodiment,"

"according to one embodiment," or "in some embodiments" in various places in the specification are not necessarily all referring to the same embodiment, nor are separate or alternative embodiments mutually exclusive of other embodiments. Moreover, various features are described which may be exhibited by some embodiments and not by others. Similarly, one or more features may be described for one embodiment which can also be reasonably used in another embodiment.

As used herein, "at least a portion" can refer to at least about 0.1%, 1%, 10%, 20%, 30%, 40%, 50%, 60%, 70%, 80,%, 90%, 99%, and 100%.

Some of the implantable devices described herein are adapted to promote a fibrotic response at a site of contact. As used herein, "fibrotic response" or "fibrosis" can refer to the formation of fibrous tissue in response to medical intervention. Implantable devices which induce a fibrotic response can do so through one or more mechanisms, for example, stimulating migration or proliferation of connective tissue cells, such as fibroblasts, smooth muscle cells, and vascular smooth muscle cells; inducing production of extracellular matrix components, such as collagen; promoting tissue remodeling; and inducing or promoting angiogenesis.

An implantable device can comprise one or more components that can include, for example, a plurality of microparticles, a biodegradable matrix, a bioactive agent, and/or a substrate. The following description provides embodiments of implantable devices and methods of using such devices.

In some embodiments, microparticles can promote a fibrotic response at the site of implantation and provide a scaffold to promote connective tissue deposition around the microparticles. Microparticles can be microspheres, and/or nanoparticles. As will be understood, microparticles may be small enough to be delivered to a site, for example, by injection, but large enough to resist phagocytosis and the lymphatic and blood system from washing away any of the microparticles. As such, microparticles can have a diameter of greater than about 10 μm. In some embodiments, the microparticles can have a diameter between about 20 μm to about 200 μm, a diameter between about 25 μm to about 100 μm, or a diameter between about 30 μm to about 50 μm. The microparticles can also be highly refined to limit any inflammation from smaller particles, and to increase the roundness and smoothness of the particles.

The microspheres can comprise an inert, histocompatible material, such as glass, hydroxapatite, powdered bone, or a polymer. The polymer can be cured and polymerized prior to implantation to reduce toxic or carcinogenic potential of the monomers or cure agents. The inert histocompatible polymer can be an acrylic polymer. The acrylic polymer can be a polymer of methacrylate or one of its esters, such as methyl methacrylate, ethyl methacrylate, n-butyl methacrylate, isobutyl methacrylate, lauryl methacrylate, and 2-ethylhexyl methacrylate or any combination or copolymer thereof. In preferred embodiments, microparticles can comprise polymethylmethacrylate (PMMA). Some embodiments in the form of a gel pr paste are described in U.S. Pat. No. 5,344,452, which is incorporated by reference in its entirety.

Microparticles can be porous or non-porous. Porous microparticles containing an additional agent may be used to deliver agents to the site of implantation.

In some embodiments, the microparticles can be suspended in a suspension agent. The suspension agent can be an aqueous or non-aqueous solution. The suspension agent can be of sufficient viscosity to promote the suspension of the microparticles. The suspension agent can be, for example, up to about 0.1%, 0.2%, 0.5%, 1.0%, 2.0%, 5.0%, 10%, 15%, 20%, 30%, 40%, 50%, 60%, 70% and 80% by volume microparticles. The amount of microparticles used is determined in part by other components of the suspension agent, such as the carrier concentration, and the method of implantation, such as injection.

The suspension agent can also contain a polymer, which can be histocompatible, as a carrier. Such a carrier can be a biodegradable matrix. A biodegradable matrix can comprise a biodegradable polymer. Examples of biodegradable polymers include collagen, albumin, gelatin, chitosan, hyaluronic acid, starch, cellulose, cellulose derivatives (e.g. methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D, L lactide), poly (D, L-lactide-co-glycolide), poly (glycolide), poly(hydroxybutyrate), poly(alkylcarbonate), poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers thereof (see generally, Ilium, L., Davids, S. S. (eds.) "Polymers in Controlled Drug Delivery" Wright, Bristol, 1987; Arshady R., "Preparation of biodegradable microspheres and microcapsules." J. Controlled Release 17:1-22, 1991; Pitt C. G., "The controlled parenteral delivery of polypeptides and proteins." Int. J. Pharm. 59:173-196, 1990; Holland et al, "Polymers for Biodegradable Medical Devices. 1. The Potential of Polyesters as Controlled Macromolecular Release Systems." J. Controlled Release 4:155-180, 1986).

In preferred embodiments, the biodegradable polymer can comprise collagen. Collagen may allow for the separation of the microspheres to allow tissue ingrowth. The collagen can be in many types and forms, or in combinations thereof. For example, collagen can be Type I, II or III. Collagen can be native, denatured or cross linked. The various types and forms of collagen are described generally in Methods in Enzymol. (1982) 82:3-217, Pt. A, incorporated by reference in its entirety. For example, collagen can be produced from animal derived tissues such as bovine or porcine hides, avian combs, human tissues such as cadaver skin or human cell cultures or through recombinant methods. In some embodiments, an implantable device can contain a collagen fully dissolved or in suspension. The solution can contain up to about 0.1%, 0.2%, 0.5%, 1.0%, 2.0%, 2.5%, 3.0%, 3.5%, 4.0%, 4.5%, 5%, 6%, 7%, 8%, 9%, 10%, 20%, 30%, 40%, 50%, 60%, 70%, or 80% (v/v) collagen content. The amount of collagen content in the solution is in part determined by the resultant viscosity, the percentage of other components such as microparticles and the method of implantation, such as injection.

In particular embodiments, an implantable device comprises a collagen matrix and microparticles. An example of a commercially available material that may be used in some embodiments includes ARTEFILL (Artes Medical Inc.). ARTEFILL comprises PMMA microparticles suspended in bovine collagen.

Other examples of commercially available materials that have been used for tissue repair and cosmetic applications include bovine collagen products such as ZYDERM I, ZYDERM II, and ZYPLAST (each produced by Allergan Inc.); bioengineered human collagen products such as COSMODERM I, COSMODERM II, and COSMOPLAST (Allegan Inc.); and porcine collagen products such as EVOLENCE (Ortho-McNeil-Janssen Pharmaceuticals, Inc.). More examples of collagen products include collagen meshes such as INSTAT (Johnson & Johnson), and composite collagen meshes such as ALLODERM (Lifecell Corp.), as well as collagen sponges such as SURGIFOAM (Johnson & Johnson) and TERUDERMIS (Terumo Corp.).

Implantable devices described herein can include additional bioactive agents. Bioactive agents can include any composition that is able to invoke a biological response in a subject. A biological response can include, for example, responses to promote healing such as a fibrotic response. Examples of bioactive agents that can induce a fibrotic response include silk, talc, chitosan, polylysine, fibronectin, bleomycin. As will be understood, in some embodiments, the microparticles can induce a fibrotic response. More examples of bioactive agents include local anesthetics (e.g. lidocaine, bupivacaine, procaine, tetracaine, dibucaine, benzocaine, p-buthylaminobenzoic acid 2-(diethylamino) ethyl ester HCl, mepivacaine, piperocaine, dyclonine, and opioids such as morphine, diamorphine, pethidine, codeine, hydrocodone, and oxycodone), non-steroidal anti-inflammatory drugs (e.g. ketoprofen, auranofin, naproxen, acetaminophen, acetylsalicylic acid, ibuprofen, phenylbutazone, indomethacin, sulindac, diclofenac, paracetamol, and diflunisal, Celecoxib, and Rofecoxib), antibiotics (e.g. clindamycin, minocycline, erythromycin, probenecid, and moxifloxacin), and antineoplastic agents. Antineoplastic agents can have antimicrobial activity at extremely low doses; examples include anthracyclines (e.g. doxorubicin and mitoxantrone), fluoropyrimidines (e.g. 5-FU), folic acid antagonists (e.g. methotrexate), podophylotoxins (e.g. etoposide), camptothecins, hydroxyureas, and platinum complexes (e.g. cisplatin). In preferred embodiments, the implantable device includes lidocaine. The concentration of lidocaine can be less than about 0.1%, 0.2%, 0.3%, 0.5%, 0.7%, 0.8%, 0.9%, 1%, and 5% by weight.

Implantable devices described herein can include a substrate. The microparticles and/or biodegradable matrix can be embedded in the substrate. In some embodiments, the microparticles and/or biodegradable matrix can coat or wrap at least a portion of the substrate. The substrate can comprise a non-biodegradable material such as, nylon, Dacron and Teflon. More examples of non-biodegradable materials that can be used with the embodiments described herein include polyamides, polyolefins (e.g. polypropylene and polyethylene), polyurethanes, polyester/polyether block copolymers, polyesters (e.g. PET, polybutyleneterephthalate, and polyhexyleneterephthalate), polyester cloth (e.g. DACRON), polyester sheeting (e.g. MYLAR; DuPont), nylon meshes, DACRON meshes (e.g. MERSILENE; Ethicon, Inc.), acrylic cloth (ORLON; DuPont), polyvinyl sponge (IVALON), polyvinyl cloth (VINYON-N), polypropylene mesh (MARLEX or BARD; CR Bard, Inc.; and PROLENE; Ethicon, Inc.), silicones, fluoropolymers (e.g. fluorinated ethylene propylene), and polytetrafluoroethylene (PTFE; e.g. TEFLON mesh and cloth; DuPont).

In some implementations, an implantable device can be a fluid, suspension, emulsion, microspheres, paste, gel, spray, aerosol, or sheet. With respect to sheets, the dimensions of a sheet can vary according to the application. Accordingly, sheets can be of varying sizes, thicknesses, geometries and densities. For applications such as capsular augmentation, the sheet can have a thickness of less than about 1 mm, 2 mm, 3 mm, 4 mm, 5 mm, and 10 mm. As will be appreciated, a sheet can be trimmed to the geometries and size appropriate to the application. In some embodiments, a sheet can be rectangular with a length sufficient to circumvent the capsule of a canine coxofemoral joint. In some embodiments, a sheet can have a length and breadth sufficient to make contact with at least a portion of the capsule of a canine coxofemoral joint.

For sheet material, woven structures are advantageous, as well as microporous materials. The implantable device may be fenestrated to promote infiltration by the host into the sheet. Such meshes can act as a scaffold. The fenestrations may be formed in a variety of geometric shapes and sizes. Initially, a fenestrated implantable device may not be as strong as a solid sheet. However, because of the increased surface area and the potential for fibrovascular infiltration through the fenestrations, a fenestrated implantable device may ultimately be stronger than a solid sheet implant. The fenestrations may also be used with sutures or other fixing devices to attach the implantable device to a site, for example, the capsule of a canine coxofemoral joint.

An implantable device including a mesh can provide many important advantages. Some mesh implants may be only as strong as the tissue in which the mesh is integrated. However, without wishing to be bound by any one theory, it is believed that when the implant includes microparticles a fibrotic response is induced in the host. In such a response, the host's response for healing occurs especially quickly along the scaffold of the implant. The microparticles make this process occur much faster than mesh implants without particles associated therewith. The body's inflammatory response to the mesh implant is such that fibrous tissue forms a capsule around the biological mesh, and, thus, provides stability and security in the repair.

As used herein "subject" can refer to an animal that can benefit from the methods and devices described herein. As will be understood by one of skill in the art, "need" is not an absolute term and merely implies that the subject can benefit from the methods and devices described herein. In preferred embodiments, the subject is a dog.

Augmentation of a coxofemoral joint may prevent, reduce, or treat various joint disorders. Disorders amenable to the methods and compositions described herein can include, for example, hip dysplasia, osteoarthritis, coxarthrosis, and chronic subluxation. More examples include chronic luxations, failed closed reductions, excessive postreduction instability, intra-articular fractures, concurrent pelvic fractures, or other fractures of the affected limb that prevent closed reduction (Martini F. M. et al., "Extra-articular absorbable suture stabilization of coxofemoral luxation in dogs." Vet Surg 30: 468-475 (2001), incorporated by reference in its entirety). Moreover, the devices and methods described herein can also be utilized in association with other methods well known in the art to promote stabilization of hip luxation (see generally, Johnson A. L. and Dunning D. Atlas of orthopedic surgical procedures of the dog and cat. Chapters 15-18 (2005), incorporated by reference in its entirety).

A subject can be identified by various methods, including, for example, by x-ray or a test that requires manipulation of the hip joint into standard positions well known in the art (see generally, Slatter, D., Textbook of Small Animal Surgery, Chapter 144 (2002), incorporated by reference in its entirety).

In addition, the methods and compositions can be used prophylactically to prevent or reduce future damage or degeneration of a joint. Subjects that may benefit from treatment can include particular types of dogs that may be more susceptible to hip dysplasia, for example, larger dogs and particular breeds such as Golden Retrievers, Labrador Retrievers, German Shepherds, Bulldogs, and St Bernards. Also, dogs with hip joint laxity may be susceptible to hip dysplasia and associated disorders. Such subjects may benefit from prophylactic treatment.

Various methods can be used to deliver an implantable device to a subject. In some embodiments, the method of delivery can be during an open surgical procedure, microdisectomy, percutaneous procedure, and/or by injection. Where an implantable device comprises a gel, paste, liquid or fluid, the device can be delivered to a site at the coxofemoral joint by injection. As will be appreciated, the size of the needle used during such injections will vary according to the subject, viscosity of the implantable device, and application. For example, the needle can have a gauge in the range of about 22 to 25, and length in the range of about 1.5 to 3.0 inches. The volume injected can be less than about 0.1 ml, 0.5 ml, 1.0 ml, 1.2 ml, 1.5 ml, 2.0 ml, 2.5 ml, 5 ml, 10 ml, 20 ml, and 50 ml. Delivery can be to one of more sites at the coxofemoral joint so that the implantable device contacts at least a portion of the coxofemoral joint. Such sites may be intra-articular or extra-articular, and can include the capsule, the stratum fibrosum of the capsule, the iliofemoral ligament, ischiocapsular ligament, pubocapsular ligament, acetabular labrum, and ligamentum teres femoris.

Several techniques can be used to guide delivery during injection. Such techniques can include, for example, fluoroscopy, ultrasound, and/or the use of anatomical landmarks only. In preferred embodiments, injections may be with the aid of a fluoroscope. In such embodiments, the implantable device can include a contrast dye to visualize delivery of the implantable device at the site of implantation.

Where an implantable device comprises a sheet, the sheet may be delivered to a site at the coxofemoral joint during an open surgical procedure, microdisectomy, and/or percutaneous procedure. As used herein, "sheet" can also refer to "mesh" in some instance. The sheet can contact at least a portion of the coxofemeroal joint at one or more sites, for example, the capsule, the iliofemoral ligament, ischiocapsular ligament, pubocapsular ligament, acetabular labrum, and ligamentum teres femoris. In some embodiments, a sheet can circumvent the coxofemoral joint, and in particular, the capsule of the coxofemoral joint. In such embodiments, the sheet may be imbricated to the capsule and stimulate tissue growth. It is envisioned that new tissue growth tightens the capsule, thus promoting containment and minimizing subluxation at the joint.

Sheets can be attached at one or more sites at a coxofemoral joint. Such sites will be apparent to a skilled artisan, and may include, the capsule, iliofemoral ligament, ischiocapsular ligament, pubocapsular ligament, acetabular labrum, ligamentum teres femoris, acetabulum, and femoral neck. Sheets can be anchored to the joint by various methods. Examples include the use of sutures, screws, anchors, hooks, staples, pins, and darts with methods well known in the art.

In certain embodiments, the coxofemoral joint may include a defect, for example, a partial capsulectomy, small capsulotomy, or large capsulotomy. The sheet can span the defect and be attached to the joint to augment the compromised capsule, for example, at the capsule at the edges of the defect. In some embodiments, the sheet can be attached to the defect. In addition, it is also envisioned that the devices described herein can be used where a coxofemoral joint has undergone complete capsulectomy. In such embodiments, a sheet can be utilized to replace the capsule and attached to the acetabulum and femoral neck of the joint.

Various modifications to these examples may be readily apparent to those skilled in the art, and the principles defined herein may be applied to other examples without departing from the spirit or scope of the novel aspects described herein. Thus, the scope of the disclosure is not intended to be limited to the examples shown herein but is to be accorded the widest scope consistent with the principles and novel features disclosed herein. Accordingly, the novel aspects described herein is to be defined solely by the scope of the following claims.

What is claimed is:

1. A method for augmenting the capsule of a coxofemoral joint in a canine subject comprising:
    identifying a canine subject in need of coxofemoral capsular augmentation;
    delivering an implantable device to said coxofemoral capsule, wherein said implantable device comprises a biodegradable matrix and a plurality of microparticles; and
    contacting said implantable device with a ligament associated with said capsule.

2. The method of claim 1, wherein said implantable device comprises a sheet.

3. The method of claim 2, wherein said sheet comprises fenestrations.

4. The method of claim 2, further comprising anchoring said implantable device at said joint.

5. The method of claim 4, wherein said anchoring is at one or more sites of said joint selected from the capsule, iliofemoral ligament, ischiocapsular ligament, pubocapsular ligament, acetabular labrum, ligamentum teres femoris, acetabulum, or femoral neck.

6. The method of claim 1, wherein said delivering comprises injecting said implantable device into one or more sites of said capsule.

7. The method of claim 6, wherein said one or more sites are selected from the capsule, iliofemoral ligament, ischiocapsular ligament, pubocapsular ligament, acetabular labrum, or ligamentum teres femoris.

8. The method of claim 6, wherein said injecting is into at least a portion of the stratum fibrosum of said capsule.

9. The method of claim 1, wherein said contacting said implantable device with at least a portion of said joint comprises at least a portion of one or more sites selected from the capsule, iliofemoral ligament, ischiocapsular ligament, pubocapsular ligament, acetabular labrum, or ligamentum teres femoris.

10. The method of claim 1, wherein said joint has undergone capsulotomy or partial capsulectomy.

11. The method of claim 1, wherein said delivering comprises percutaneous delivery.

12. The method of claim 1, wherein said delivering comprises an open surgical procedure.

13. The method of claim 1, wherein said biodegradable matrix comprises bovine collagen.

14. The method of claim 1, wherein said biodegradable matrix comprises one or more materials selected from albumin, gelatin, chitosan, hyaluronic acid, starch, cellulose, cellulose derivatives (e.g. methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D, L lactide), poly (D, L-lactide-co-glycolide), poly(glycolide), poly(hydroxybutyrate), poly(alkylcarbonate), poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers thereof.

15. The method of claim 1, wherein said plurality of microparticles comprise a material selected from the group consisting of poly methacrylate, polymethyl methacrylate, hydroxapatite, powdered bone, and glass.

16. The method of claim 1, wherein said plurality of microparticles are substantially spherical with a diameter less than 200 μm.

17. The method of claim 16, wherein said plurality of microparticles are substantially spherical with a diameter less than 100 μm.

18. The method of claim 1, wherein said implantable device further comprises a bioactive agent.

19. The method of claim 18, wherein said bioactive agent comprises an agent selected from the group consisting of a local anesthetic, non-steroidal anti-inflammatory drug, antibiotic, and antineoplastic agent.

20. The method of claim 18, wherein said bioactive agent comprises lidocaine.

21. The method of claim 1, wherein said implantable device further comprises a substrate.

22. The method of claim 21, wherein said substrate comprises a material selected from nylon, Dacron, and Teflon.

23. The method of claim 21, wherein said substrate is coated with said plurality of microparticles and said biodegradable matrix.

24. A method for augmenting the capsule of a coxofemoral joint in a canine subject comprising:
    identifying a canine subject in need of coxofemoral capsular augmentation;
    wrapping an implantable sheet around a coxofemoral capsular ligament, wherein the implantable sheet comprises a biodegradable matrix and a plurality of microparticles.

25. The method of claim 24, further comprising anchoring the sheet at the joint.

26. The method of claim 24, wherein the biodegradable matrix comprises bovine collagen.

27. The method of claim 24, wherein the biodegradable matrix comprises one or more materials selected from albumin, gelatin, chitosan, hyaluronic acid, starch, cellulose, cellulose derivatives (e.g. methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D, L lactide), poly (D, L-lactide-co-glycolide), poly(glycolide), poly(hydroxybutyrate), poly(alkylcarbonate), poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers thereof.

28. The method of claim 24, wherein the plurality of microparticles comprise a material selected from the group consisting of poly methacrylate, polymethyl methacrylate, hydroxapatite, powdered bone, and glass.

\* \* \* \* \*